US006482615B2

(12) United States Patent
Tal et al.

(10) Patent No.: US 6,482,615 B2
(45) Date of Patent: Nov. 19, 2002

(54) METHOD AND APPARATUS FOR EFFECTING RAPID THERMAL CYCLING OF SAMPLES IN MICROTITER PLATE SIZE

(75) Inventors: Michael Tal, Kfar Bilu (IL); Joshua Livneh, Kfar Bilu (IL); Yoram Liran, Rehovot (IL)

(73) Assignee: Integrated Genetic Devices Ltd., Nes Ziana (IL)

( * ) Notice: Subject to any disclaimer, the term of this patent is extended or adjusted under 35 U.S.C. 154(b) by 0 days.

(21) Appl. No.: 09/846,182

(22) Filed: May 2, 2001

(65) Prior Publication Data

US 2002/0123131 A1 Sep. 5, 2002

Related U.S. Application Data

(63) Continuation-in-part of application No. 09/796,542, filed on Mar. 2, 2001, now abandoned.

(51) Int. Cl.[7] .......................... C12P 19/34

(52) U.S. Cl. ............... 435/91.2; 435/286.6; 435/303.1; 422/110; 219/635; 219/400; 236/3; 935/77; 935/85

(58) Field of Search ....................... 435/91.2, 285.1, 435/286.6, 287.2, 303.1; 422/110, 131; 935/77, 78, 85, 88; 236/3, 91 A; 219/635, 663, 400

(56) References Cited

U.S. PATENT DOCUMENTS

| | | | | | |
|---|---|---|---|---|---|
| 3,616,264 | A | * | 10/1971 | Ray et al. | 237/3 |
| 4,420,679 | A | * | 12/1983 | Howe | 126/21 A |
| 5,187,084 | A | * | 2/1993 | Hallsby | 435/286.6 |
| 5,455,175 | A | * | 10/1995 | Wittwer et al. | 422/104 |
| 5,783,439 | A | * | 7/1998 | Reichler et al. | 435/286.1 |
| 5,942,432 | A | * | 8/1999 | Smith et al. | 165/61 |

* cited by examiner

*Primary Examiner*—David A. Redding
(74) *Attorney, Agent, or Firm*—G.E. Ehrlich Ltd,

(57) ABSTRACT

A method and apparatus for effecting rapid thermal cycling of samples, by producing a high-velocity air flow through a closed loop flow path, and energizing an electrical heater within the closed loop flow path to heat the air flowing therethrough to a desired temperature. A sample holder is introduced into the closed loop flow path for exposing the sample holder to the high-velocity heated air flowing therethrough for rapidly heating the sample. The sample is rapidly cooled to a desired temperature by de-energizing the electrical heater, and opening an air outlet from the closed loop flow path, while continuing to produce the high-velocity air flow therethrough.

26 Claims, 7 Drawing Sheets

METHOD AND APPARATUS FOR EFFECTING RAPID THERMAL CYCLING OF SAMPLES IN MICROTITER PLATE SIZE

RELATED APPLICATION

The present application is a continuation-in-part of application Ser. No. 09/796,542, filed Mar. 2, 2001, and expressly abandoned Aug. 1, 2002.

FIELD AND BACKGROUND OF THE INVENTION

The present invention relates to a method and apparatus for effecting rapid thermal cycling of samples. The invention is particularly useful in a process called "Polymerase Chain Reaction", or PCR, in a biological process called Cyclic DNA Amplification, and is therefore described below particularly with respect to this application, but it will be appreciated that the invention could advantageously be used in other applications involving the heating and/or cooling of samples.

The PCR process involved in Cyclic DNA Amplification requires rapidly varying the temperature of a plurality of samples repeatedly through predetermined temperature cycles in a precisely controlled manner. Existing thermal cyclers can generally be divided into two main categories: (a) cyclers based on thermal blocks into which the samples are introduced and which are heated and cooled by Peltier elements; and (b) cyclers based on the circulation of air, water or other fluids.

In the case of thermal-block cyclers using Peltier elements, the large thermal mass of the block causes the heating/cooling process to be slow. A typical 30/cycle PCR process based on this technique generally takes about 2–2.5 hrs to complete. Another disadvantage of the block-cyclers is the difficulty in pulling the sample holders (e.g., microtiter plates) out of the block at the end of the process because of the deformation of the sample holders, usually plastic wells, caused by the temperature variations. Such deformations make it difficult to interface the cycler with robots which are generally needed for high-throughput processing.

Thermal cyclers using water baths have also been used for this purpose, but the high thermal mass of the water also extends the time required for a complete heating/cooling cycle, such that a 30-cycle PCR process also takes a substantial period of time to complete.

Various types of thermal cyclers based on the circulation of air have been proposed, such as described for example in U.S. Pat. Nos. 3,616,264, 4,420,679 and 5,455,175, but the previously known thermal cyclers of this type have not been found completely satisfactory for efficiently, rapidly and uniformly carrying out the PCR process, and/or do not allow standard sample holders of the rectangular matrix type, such as the microtiter plate, to be conveniently used.

OBJECTS AND BRIEF SUMMARY OF THE INVENTION

An object of the present invention is to provide a novel method and apparatus for effecting rapid and uniform thermal cycling of samples, particularly a plurality of samples arranged in microtiter format. Another object of the invention is to provide a method and apparatus of the foregoing type particularly useful in the PCR process for DNA amplification and for cycle-sequencing.

According to one aspect of the present invention, there is provided a method of effecting rapid thermal cycling of samples, comprising: producing a high-velocity laminar air flow through a channel defining a closed loop flow path; energizing an electrical heater within the closed loop flow path to heat the air flowing therethrough to a desired temperature; introducing a sample holder containing at least one sample into a section of the closed loop flow path for exposing the sample holder to the high-velocity heated air flowing therethrough for rapidly heating the sample; and rapidly cooling the sample to a desired temperature by de-energizing the electrical heater, and opening an air outlet from the closed loop flow path, while continuing to produce the high-velocity air flow through the channel.

According to a further feature in the described preferred embodiment, the channel is of rectangular cross-section. This features aids in producing a uniform heating and/or cooling of the samples.

According to further preferred features, the channel defining the closed loop flow path is a closed loop channel having a selectively-openable inlet and a selectively-openable outlet.

Preferably, the air velocity is 10–30 m/sec at 25° C. This has been found to produce laminar air flow with uniform heating/cooling of the samples in a microtiter-size sample holder.

According to further features in other described preferred embodiments, the section of the closed loop flowpath into which the sample holder is introduced is of decreasing cross-sectional area from the upstream side of the sample holder to the downstream side of the sample holder, to produce an increase in the velocity of the airflow at the downstream side as compared to that at the upstream side. Such an arrangement may be provided, for example, to compensate for the "shading effect" that may be produced with respect to the airflow from the upstream side to the downstream side of the sample holder where there is a relatively small spacing between the individual holders.

In one described embodiment, the decreasing cross-sectional area is effected by the provision of an inclined baffle in the section of the closed loop flow path into which the sample holder is introduced, the inclined baffle underlying the sample holder. In another described preferred embodiment, the decreasing cross-sectional area is effected by mounting the sample holder in an inclined position in the section of the closed loop flowpath.

According to a further feature in the preferred embodiment described below, the holder includes a cover containing another electrical heater which may be also energized during the thermal cycling process in order to prevent excess vaporization of the samples.

According to another aspect of the present invention, there is provided apparatus for effecting rapid thermal cycling of samples, comprising: a housing including a channel defining a closed loop flow path; an air impeller within the housing for producing a high-velocity laminar air flow through the closed loop flow path; an electrical heater within the housing for heating the air flowing through the closed loop flow path to a desired temperature; an access opening in a section of the channel for introducing a sample holder containing at least one sample into a sample compartment in the closed loop flow path for exposure to the high-velocity heated air flowing therethrough; and control means for selectively energizing the electrical heater to rapidly heat the sample by the heated air flowing through the closed loop flow path, and for selectively de-energizing the electrical heater and opening the closed loop flow path with respect to the atmosphere to rapidly cool the sample.

According to further features in the described preferred embodiment, the channel comprises a first section including first and second legs parallel to each other and joined by a first U-shaped juncture, and a second section including third and fourth legs parallel to each other and joined by a second U-shaped juncture; the first and second legs of the first section being perpendicularly joined to the third and fourth legs of the second section to define a closed loop flow path constituted of two U-shaped loops perpendicularly joined to each other. Such a folded construction provides a compact, space-saving arrangement for the closed loop flow path.

According to yet another aspect of the present invention, there is provided apparatus for effecting rapid thermal cycling of samples, comprising: a housing including a channel defining a closed loop flow path for air; an impeller within the housing for producing a high velocity air flow through the closed loop flow path; an electrical heater within the housing for heating the air flowing through the closed loop flow path to a desired temperature; an access opening in a section of the channel for introducing a sample holder containing at least one sample into a sample compartment in the closed loop flow path for exposure to the high-velocity heated air flowing therethrough; and a control means for selectively energizing the electrical heater to rapidly heat the sample by the heated air flowing through the closed loop flowpath, and for selectively de-energizing the electrical heater and opening the closed loop flow path with respect to the atmosphere to rapidly cool the sample; the section of the closed loop flow path into which the sample holder is introduced being of decreasing area from the upstream side of the sample holder to the downstream side of the sample holder, to produce an increase in the velocity of the airflow at the downstream side as compared to that at the upstream side.

Further features and advantages of the invention will be apparent from the description below.

BRIEF DESCRIPTION OF THE DRAWINGS

The invention is herein described, by way of example only, with reference to the accompanying drawings, wherein.

DESCRIPTION OF THE ILLUSTRATED PREFERRED EMBODIMENT

Figure 1:
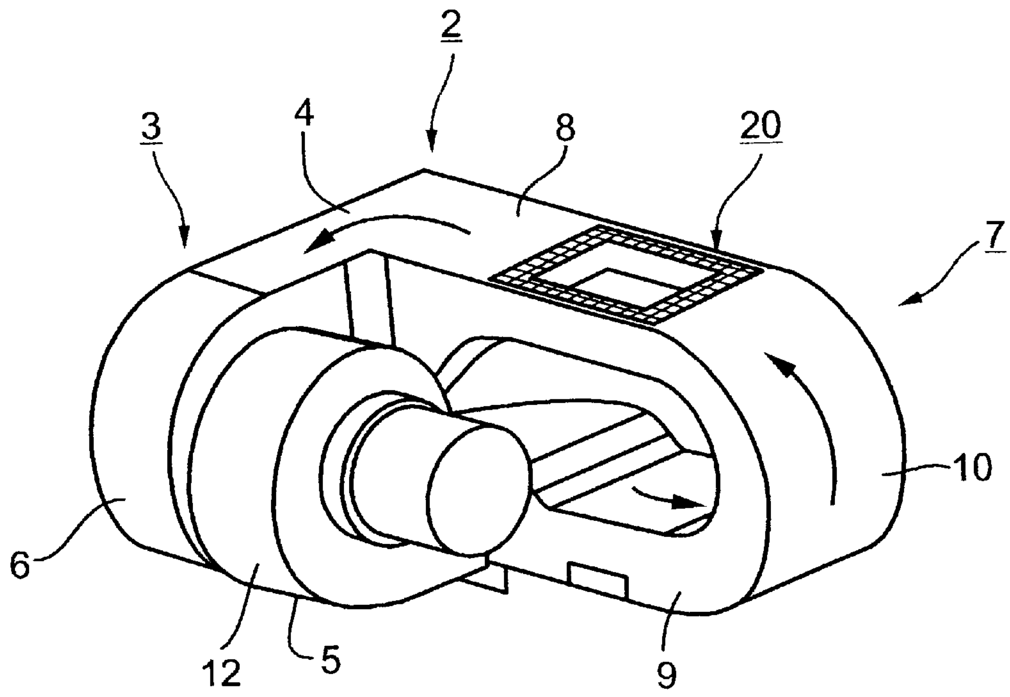
FIG. 1 is a front perspective view illustrating one form of apparatus constructed in accordance with the present invention.
Figure 2:
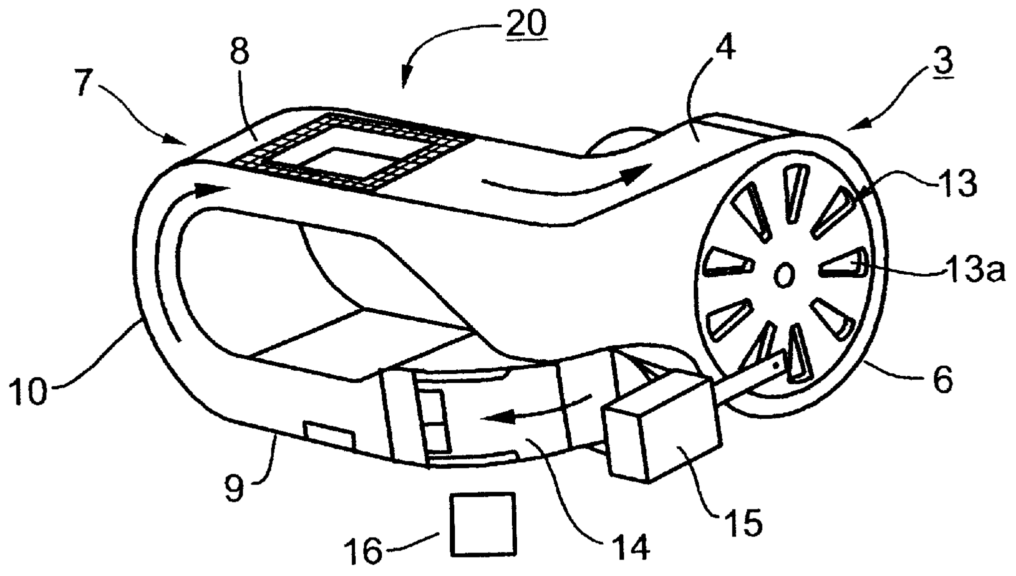
FIG. 2 is a rear perspective view of the apparatus of FIG. 1.

The thermal cycling apparatus illustrated in the drawings comprises a housing 2 defining a closed loop channel constituted of a first section, generally designated 3, including a first leg 4, and a second leg 5 parallel to leg 4 and joined to it by a U-shaped juncture 6. Housing 2 includes a second section, generally designated 7, constituted of a third leg 8, and a fourth leg 9 parallel to leg 8 and joined to it by a second U-shaped juncture 10. Legs 4 and 5 of housing section 3 are perpendicularly joined to legs 8 and 9 of housing section 7, such that the two housing sections 3 and 7 are joined to each other in an L-configuration.

Figure 3:
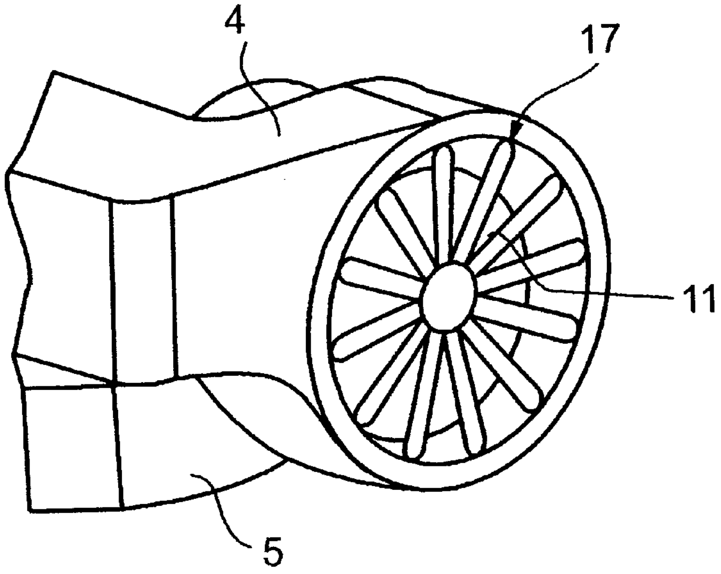
FIG. 3 illustrates the main electrical heater in the apparatus.

All of the foregoing legs 4, 5, 8, 9, as well as their respective U-shaped junctures 6 and 10, are of a channel configuration such that when the two housing sections 3, 7 are joined to each other as described above, they define a continuous closed loop flow path 11 (FIG. 3) constituted of two U-shaped loops joined perpendicularly to each other to produce a folded closed loop for space-saving purposes.

Housing section 3 includes an air impeller 12, in the form of centrifugal blower, for producing a high-velocity air flow through the closed loop channel. Housing section 3 further includes an air inlet normally closed by a rotatable plate 13 which may be selectively opened to draw air from the atmosphere into the closed loop flow path 11, and an air outlet normally closed by a pivotal or slidable door 14 which also may be selectively opened for outletting the air from the closed loop channel to the atmosphere. Air inlet 13 may be designed or controlled to be fully open at all times, whereas air outlet 14 may be partially opened to have atmospheric air enter the channel via the inlet also during the heating stage of the cycle to provide one means to control the temperature in the closed loop flow path 11.

Air inlet 13 is a rotatable plate formed with a plurality of openings *13a*alignable with corresponding openings (not seen) in an end wall of housing section 3 when the plate is rotated to its open position, and disalignable with the openings in the housing section end wall when the plate is rotated to its closed position. The air inlet plate 13 is rotatable to its open or closed position by any suitable means, such as by a solenoid, electric motor or pneumatic piston schematically shown at 15.

The air outlet 14 is in the form of a slidable or pivotal plate which is actuated by another solenoid, electric motor or pneumatic piston 16 either to its closed position for maintaining the high-velocity air flow through the closed loop flow path, to its open position for exhausting the air from that flow path to the atmosphere, or to a partially open position to control the temperature of the air within the closed loop flow path.

Housing 2 further includes an electrical heater 17 (FIG. 3) for heating the air flowing through the closed loop flow path 11 to a desired temperature, and a temperature sensor 18 (FIG. 5) for controlling the heater to produce the desired temperature. Heater 17 is of annular configuration and circumscribes the closed loop flow path 11.

Figure 4:
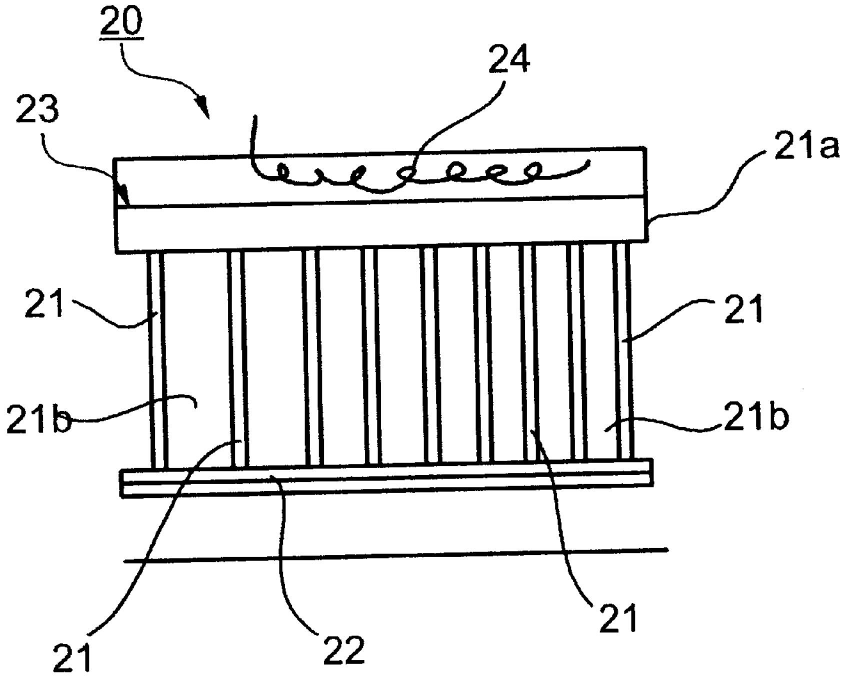
FIG. 4 illustrates the sample holder.

Leg 8 of the housing 2 is formed with an access opening for introducing a sample holder, generally designated 20, containing the samples to be heated and cooled. Sample holder 20 is preferably as described in co-pending U.S. patent application 09/339,865, assigned to the same assignee as the present application. As shown in FIG. 4, this sample holder holds a plurality of widely-spaced stainless steel tubes 21 supported in a mounting member **21*a* and arrayed in a rectangular matrix (e.g., 12×8). Each tube is of 0.86 mm internal diameter and 30 mm length and is separated from the adjacent tubes by a relatively large space 21*b*. Such a sample holder provides a large surface-to-volume ratio, and allows high heat transfer through the tube walls to the samples. Preferably, the portion of the closed loop flow path 11 defined by the housing leg 8 is of rectangular configuration and has a transverse dimension slightly larger than the transverse dimension of the sample holder 20, to define an air flow space between the housing and the sample holder on each of the opposite sides of the sample holder. Preferably, temperature sensor 18 (FIG. 5**) is just upstream of the sample holder.

Figure 5:
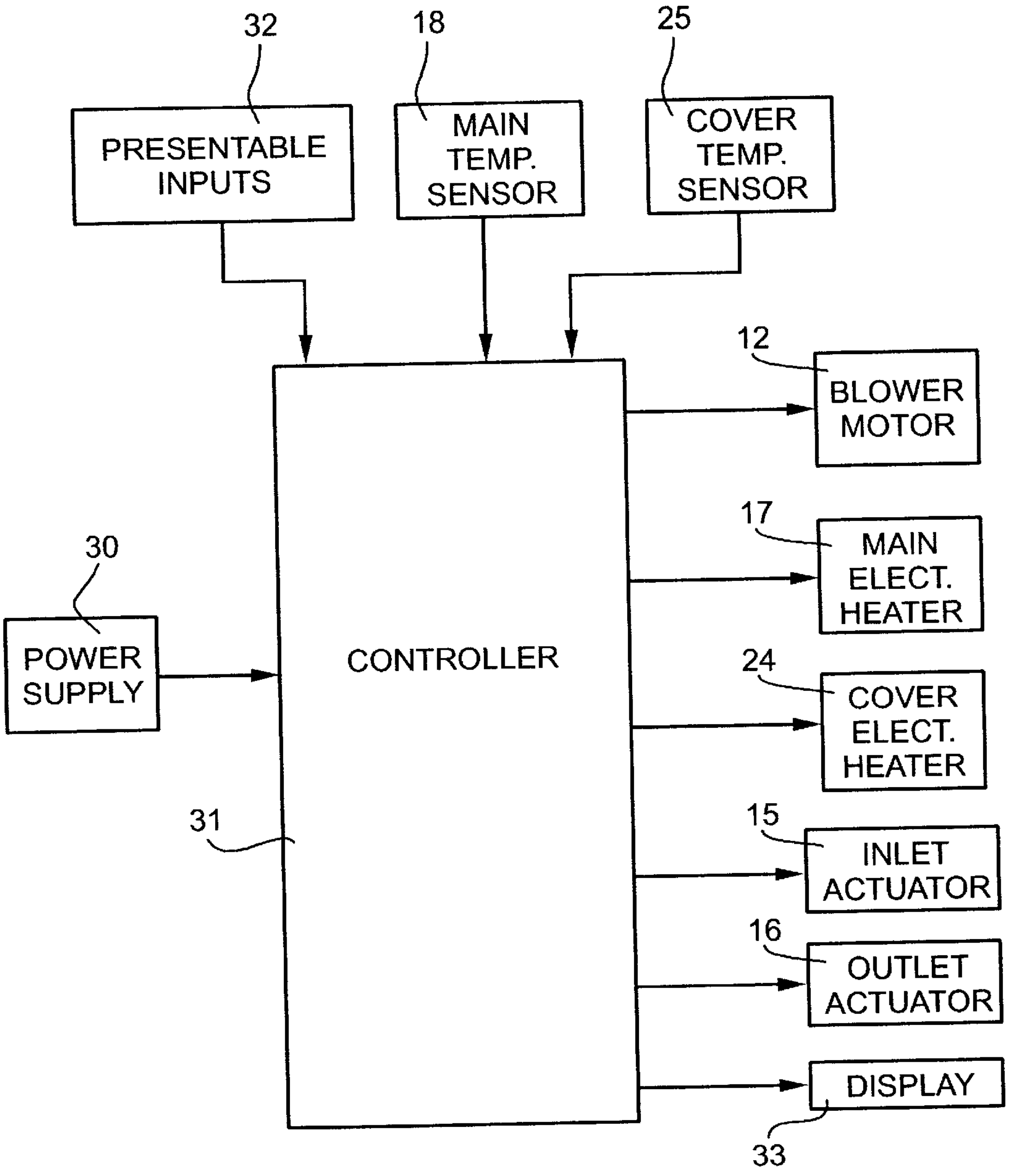
FIG. 5 is a block diagram illustrating the electrical system in the apparatus of FIG. 1.

As further shown in FIG. 4, the sample holder compartment 20 further includes a silicon rubber mat 22 engaging the open ends of the plurality of tubes 21, and a cover 23 overlying the sample holder in order to press the sample holder against the mat. The sample holder cover 23 also includes an electrical heater 24 controlled by a temperature sensor 25 (FIG. 5). The heater may be energized to keep the temperature above the sample holder at 101–110° C. in order to reduce evaporation of the samples contained in the tubes.

FIG. 5 is a block diagram illustrating the overall control system. The illustrated system includes a power supply 30 and a controller 31 which controls the various electrical devices described above, particularly the blower motor 12, the main electric heater 17, the cover electrical heater 24, the inlet actuator 15, and the outlet actuator 16. Controller 31 controls the foregoing elements according to presettable inputs, as shown at 32, the main temperature sensor 18, and the cover temperature sensor 25. The presettable inputs 32, which may be pre-programmed, determine all the control parameters for any particular process, including the air velocity, the heating temperature, the heating and cooling rates, the duration of each heating and/or cooling period, the number of cycles, and the like. The various parameters may be displayed in a display, generally designated 33, also controlled by the controller 31.

The manner in which the illustrated apparatus effects rapid thermal cycling of the samples contained within the sample holder 20 will be apparent from the above description. Thus, when samples are to be thermally cycled, the samples are introduced into the tubes 21 of the sample holder 20, and the sample holder is introduced into the closed loop flow path 11 defined by housing sections 3 and 7, via the access opening in housing leg 8. The sample holder is pressed against the mat 22 by the sample-holder compartment cover. Solenoid 15 is actuated to rotate the inlet plate 13 to close the inlet openings 13*a;* and similarly solenoid 16 is actuated to close the outlet 14. Thus, the air flow path 11 produced within the two sections 3 and 7 of housing 2 is a closed loop flow path.

Blower motor 12 is then energized in order to produce a high-velocity air flow through the closed loop flow path 11. In addition, the main electrical heater 17 is energized in order to heat the air flowing through the closed loop flow path, such that the hot air flows in the form of a laminar stream through housing leg 8 and through the spaces 21*b* between the tubes 21 of the sample holder 20 to uniformly heat the samples within the tubes. The cover heater 24 may also be energized.

The temperatures produced by the main electrical heater 17 and the cover electrical heater 24 are controlled by controller 31 in response to their respective temperature sensors 18 and 25.

When a predetermined heating cycle has been completed as controlled by controller 31, the electrical heater 17 is de-energized, and the inlet actuator 15 and outlet actuator 16 are actuated to respectively open the inlet 13 and outlet 14, while the blower motor 12 continues to operate. Thus, the housing sections 3 and 7 no longer define a closed loop flow path, but rather the flow path is open at its opposite ends to the atmosphere, such that the cool air from the atmosphere is caused to flow at a high velocity through the sample holder 20 to rapidly cool the samples therein.

After the cooling period has been completed, as controlled by the controller 31, the inlet and outlet are again closed to re-establish the closed loop flow path; and the heater 17 is re-energized to heat the high-velocity air flowing through the flow path, and thereby to heat the samples within the sample holder 20, for a new heating cycle as controlled by the controller 31.

A temperature gradient in the direction of air flow can be achieved by reducing the air velocity through the closed loop flow path 11. This temperature gradient is sometimes needed by the user of the apparatus for the optimization of the PCR process.

Test Results

In order to test the machine, measurements were made of the cycle period, temperature repeatability in consecutive cycles, and temperature uniformity between samples in the same cycle. The temperature measurements were performed by placing thin thermocouples (T-type, G-23) inside thin-wall glass capillaries of 0.8 mm internal diameter ("test tubes"). The capillaries were filled with distilled water and their bottom was sealed. The test tubes were positioned in a plate placed at the top of the process chamber so that they were dipped in the air-flow. Temperature and time measurements were performed by a VirtualBench logger model NI 4351 by National Instruments.

The cycle period and temperature repeatability were measured in a single test tube. For the temperature uniformity measurement, 9 test tubes were placed in positions covering the whole area of a microtiter plate (105×70 $mm^2$).

Figure 6:
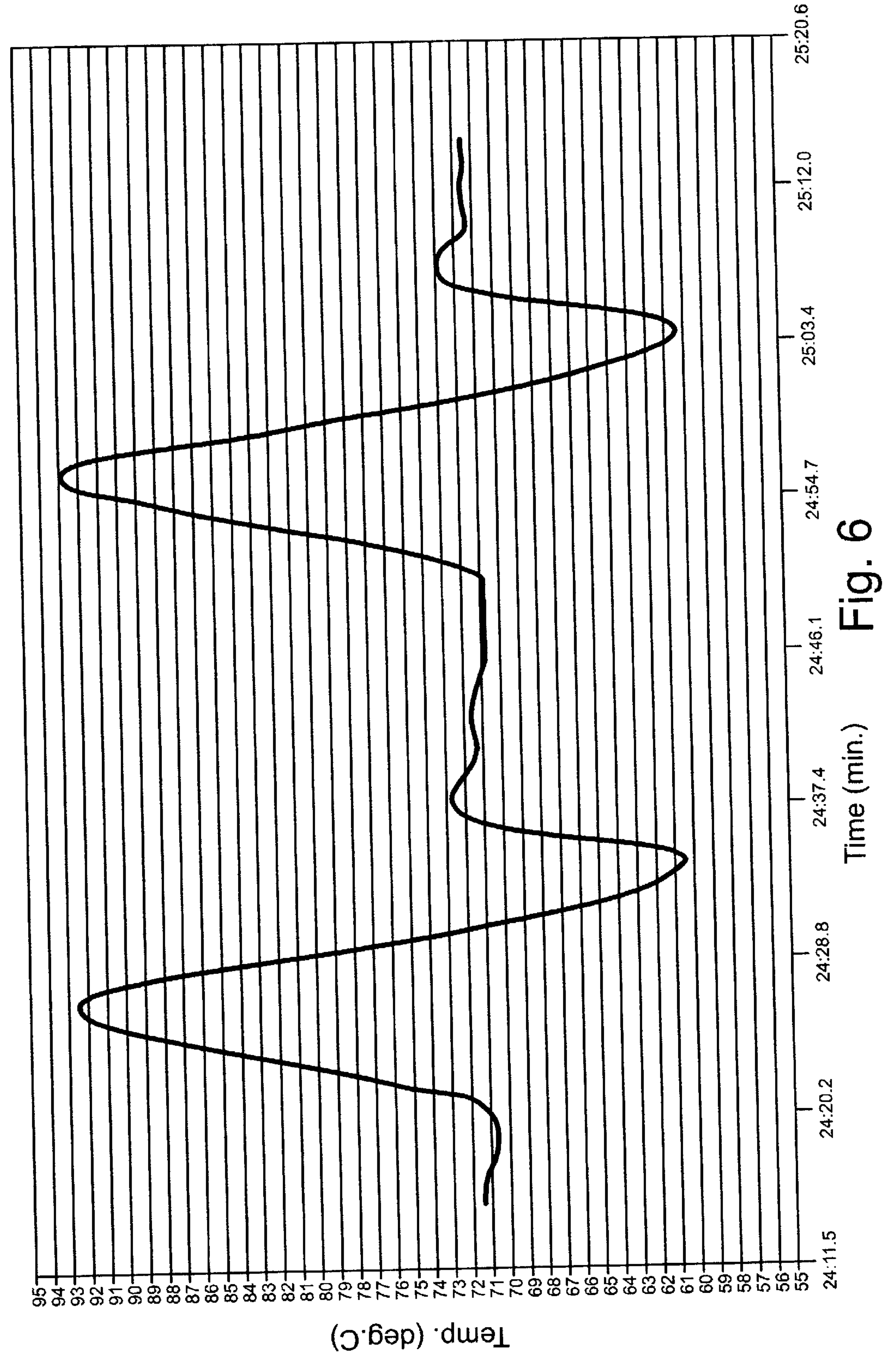
FIGS. 6–8 illustrate test results produced with the illustrated apparatus.

FIG. 6 shows the temperature profile of a single test tube positioned in the center of the plate. The temperature and time fixing were: 2 sec. in 92° C.; 2 sec. in 61° C.; and 15 sec. in 71° C. As can be seen, the total cycle period was 31 sec. and the average temperature slope over one period was 6° C./sec.

Figure 7:
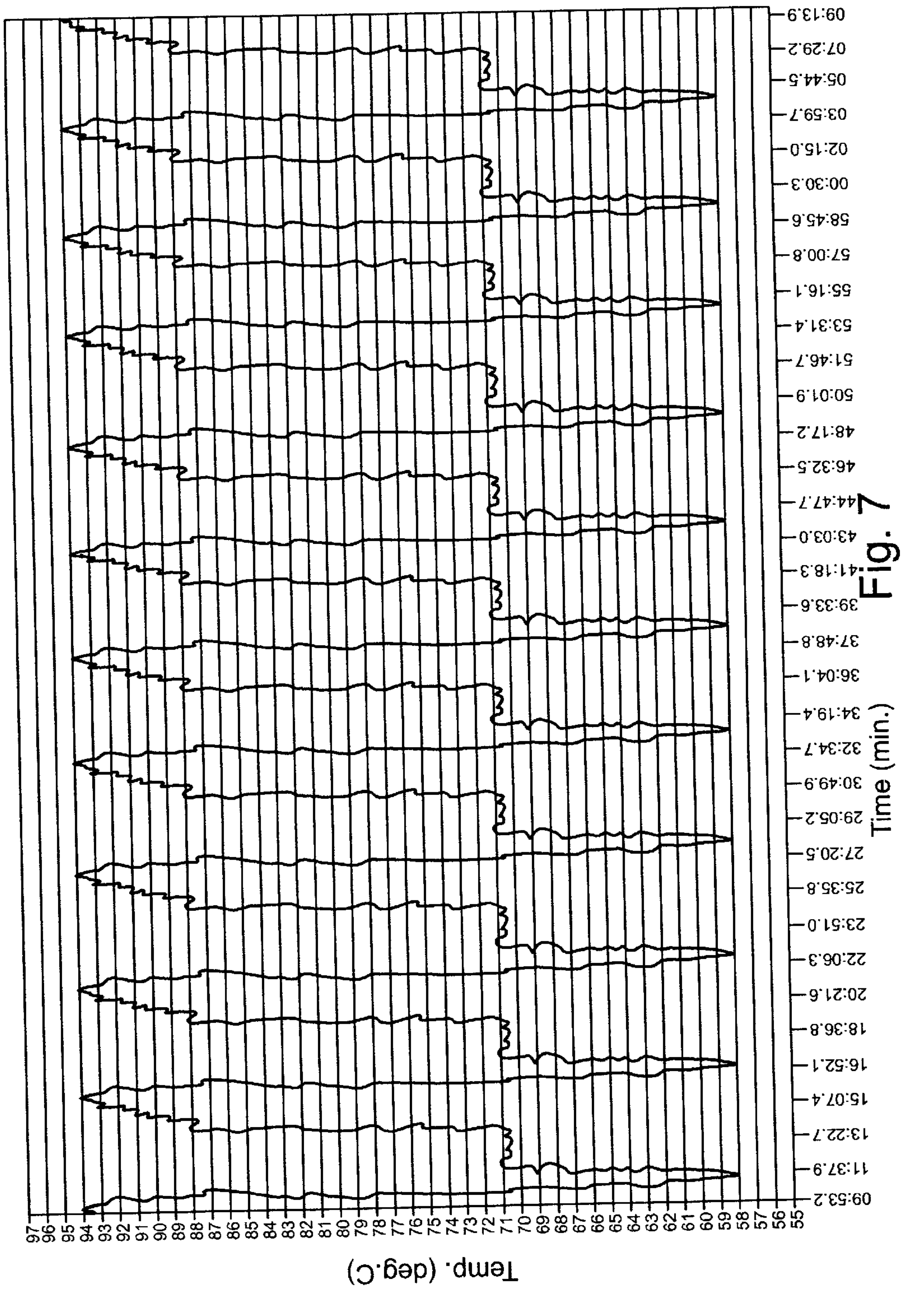

FIG. 7 shows 16 out of a total of 30 cycles. The maximum temperature variation between cycles was less than 0.5° C.

Figure 8:
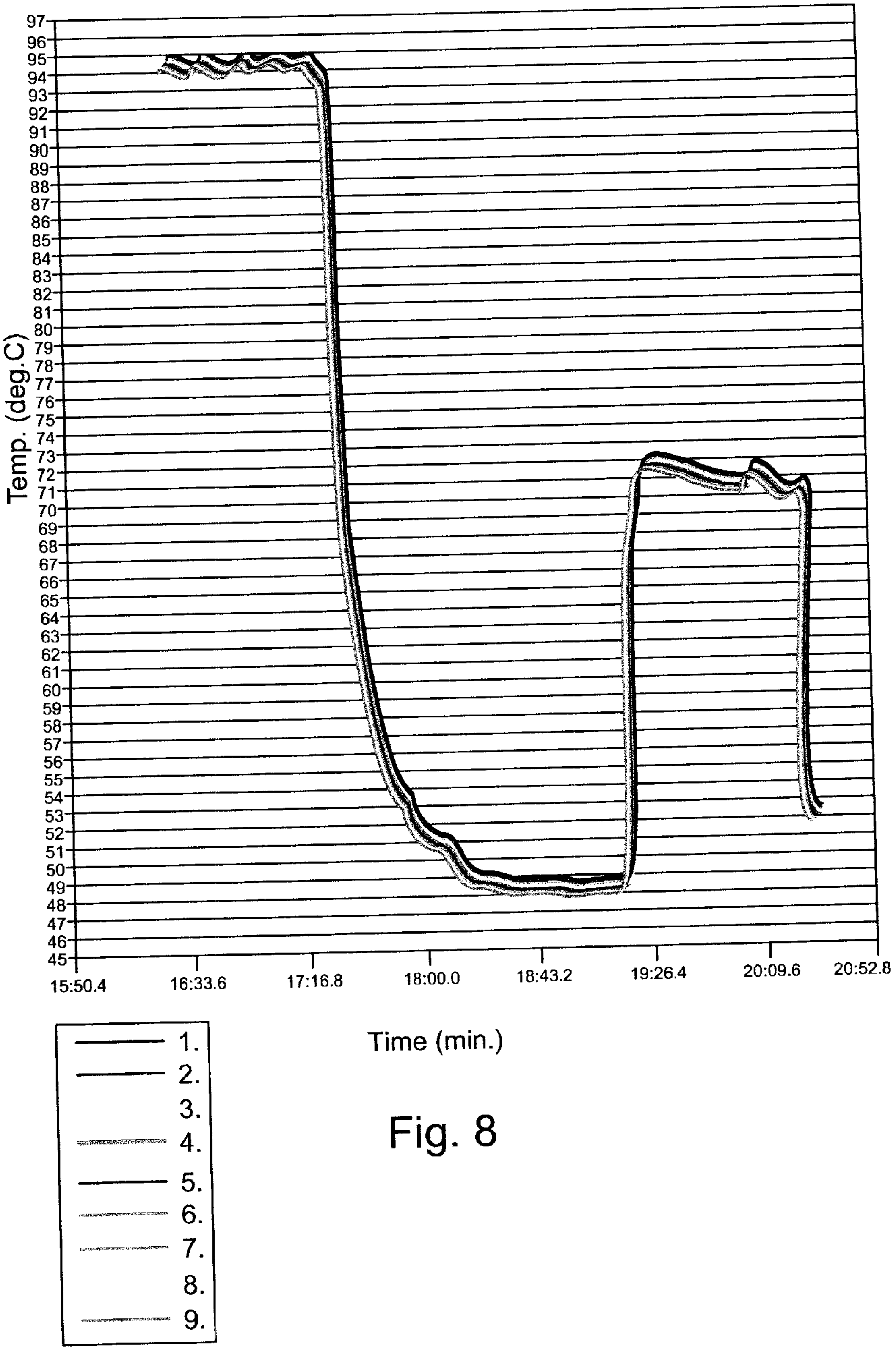

FIG. 8 shows a uniformity measurement performed by placing 9 test capillaries with thermocouples in various positions in the plate, covering the whole microtiter plate area. As can be seen, the variation between measurements was less than ±0.5° C.

As indicated above, the sample holder illustrated in FIG. 4 provides a large spacing 21*b* between the sample tubes 21 compared to the tube diameter. The ratio between tube center spacing to tube diameters has to be more then 4:1, preferbly 7:1. In such an arrangement, the airflow is substantially laminar and has substantially the same velocity at the downstream end of the sample holder 20 as at the upstream end.

However, where the apparatus is to be used with sample holders having considerably less space between the individual holders, the upstream holders tend to produce a "shading effect" with respect to the airflow towards the downstream holders, which could cause the temperature in the downstream holders to lag behind that in the upstream holders. This "shading effect" is particularly significant in microtiter plate holders in which the samples are held in a matrix of wells having a ratio between the well centers and well diameters of less than 2:1.

Figure 9:
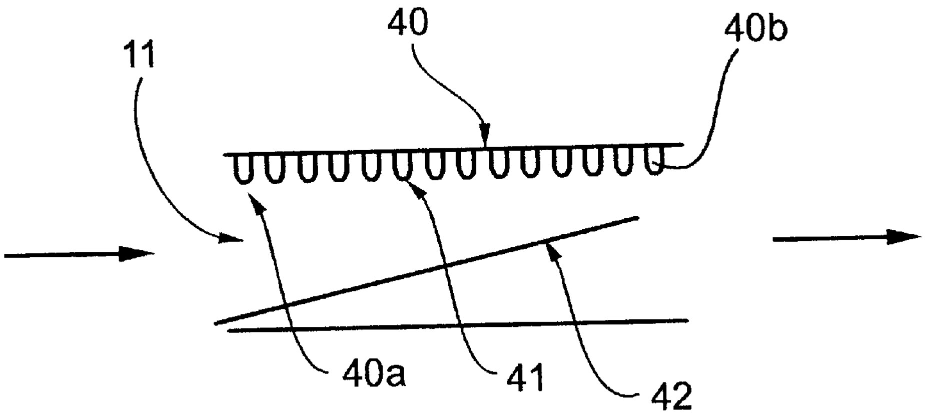
FIG. 9 illustrates one manner of compensating for the "shading effect" produced with sample holders having relatively small spacing between the individual holders.

FIG. 9 illustrates a modification in the construction of the apparatus that may be used to eliminate or substantially reduce this "shading effect".

In FIG. 9, the sample holder, therein generally designated 40, is provided with a matrix of wells 41 for holding the individual samples, with each well being of a substantially larger diameter than the tubes 21, and of substantially smaller spacing between them, than the spacing 21*b* in FIG. 4. For example, the ratio between the tube-center-spacing and the tube diameters in FIG. 4 is greater than 7:1; whereas the ratio between the well center-spacing and well diameters in FIG. 9 is less than 2:1.

In such case, the above-described "shading effect" would be very significant and would cause the temperature changes at the downstream side to lag the upstream side. To compensate for this, the section of the closed loop flowpath 11 into which the sample holder 40 is introduced is provided with a baffle 42 upwardly inclined from the upstream side 40*a* of the sample holder to the downstream side 40*b* to reduce the cross-sectional area of the air flow channel towards the downstream side.

Thus, assuming the air blower can overcome the additional load, the air velocity will be inversely proportional to the channel cross-section; that is reducing the cross-section will increase the air velocity.

The heat transfer from the air to the wall of the well 41 is by convection.

The convection rate is given by:

$$hc=0.332\ Pr^{0.33}Re^{0.6}k/D$$

Where:

Pr—is the Prendtel number.

k—is the air conductivity

D—is the diameter of the well

Re—is the Reinolds number, given by:

$$Re=VD\rho/\mu$$

V—is the air velocity $\mu$—is the air viscosity $\rho$—is the air density

It can be seen from the above equation that the convection heat transfer rate is proportional to $V_{0.6}$. Accordingly, increasing the air velocity at the downstream wells 41 compared to the upstream wells, increases heat transfer rate to the downstream wells and thereby compensates for the thermal lag produced by the above-described "shading effect".

Figure 10:
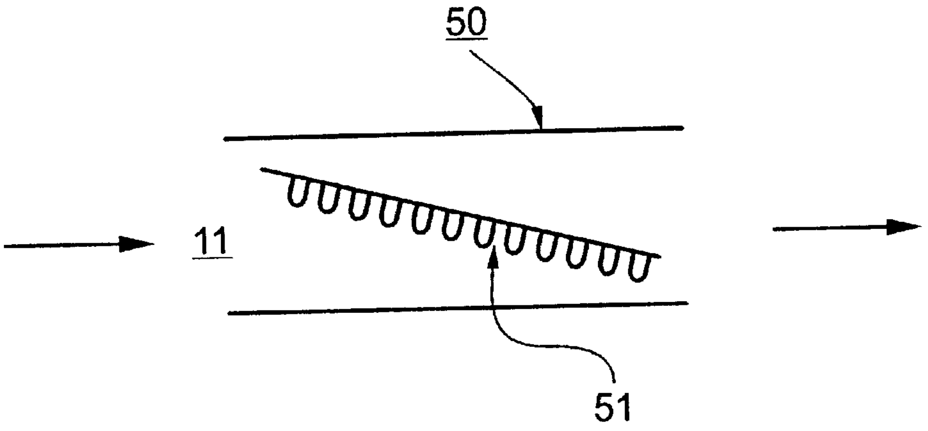
FIG. 10 illustrates another manner of compensating for such "shading effect".

FIG. 10 illustrates another manner that may be used for compensating for the above-described "shading effect". In the arrangement illustrated in FIG. 10, the sample holder, therein generally designated 50, mounts the individual sample holders 51 (e.g., wells) in a downwardly-inclined position within the section of the closed loop flowpath 11 receiving the sample holders, so as also to produce an increase in the velocity of the airflow at the downstream side of the sample holder as compared to that at the upstream side.

While the invention has been described with respect to one preferred embodiment, it will be appreciated that this is set forth merely for purposes of example, and that many variations and other applications of the invention. may be made. For example, the channel sections defining the closed loop flow path could include small aerodynamic profilers or shaped surfaces formed in, or attached to, the channel walls, to better assure high velocity laminar flow substantially perpendicular to the sample walls producing efficient and uniform heat transfer to the samples. As indicated earlier, the inlet opening could always be opened, since a closed loop flow path is still produced if the outlet alone is closed. For maximum cooling, preferably both the inlet and outlets are opened. As also indicated earlier, the outlet could be partially opened also during a heating cycle to control the temperature. The temperature can also be controlled by cyclically energizing and de-energizing the electrical heater according to a working cycle corresponding to the temperature desired. Other electrical heater could be used, and could be placed at other locations within the closed loop channel.

In addition, other sample holders could be used, for example plates formed with a rectangular matrix of wells for the samples (e.g., such as in 384-microtiter plates), but in such case the heat transfer would be less efficient, and therefore each cycle would tend to be longer. An air velocity of 10–30 m-sec at 25° C. through housing leg 8 has been found to be preferred in order to produce uniform heating/cooling together with laminar flow, but such an air velocity may be increased or decreased according to the requirements of particular applications.

While the invention has been described with respect to heating and cooling biological samples particularly in the above-described PCR process, it will be appreciated that the apparatus could be used for heating and/or cooling other types of samples.

Many other variations, modifications and applications of the invention will be apparent.

What is claimed is:

1. A method of effecting rapid thermal cycling of samples, comprising:

producing a high-velocity laminar air flow through a channel defining a closed loop flow path;

energizing an electrical heater within said closed loop flow path to heat the air flowing therethrough to a desired temperature;

introducing a sample holder containing at least one sample into a section of said closed loop flow path for exposing said sample holder to the high-velocity heated air flowing therethrough for rapidly heating the sample;

and rapidly cooling the sample to a desired temperature by de-energizing said electrical heater and opening an air outlet from said closed loop flow path, while continuing to produce said high-velocity airflow through the channel.

2. The method according to claim 1, wherein said section of the closed loop flow path into which the sample holder is introduced is of rectangular cross-section.

3. The method according to claim 1, wherein said channel defining said closed loop flow path is a closed loop channel having a selectively-openable inlet and a selectively-openable outlet.

4. The method according to claim 1, wherein said sample holder is introduced into a sample-holder compartment including a cover containing another electrical heater which may be energized during the process to reduce excessive vaporization of the sample.

5. The method according to claim 1, wherein the air flow velocity is controlled to produce a temperature gradient across the sample holder.

6. The method according to claim 1, wherein said section of the closed loop flow path into which said sample holder is introduced, has a transverse dimension slightly larger than that of a said sample holder to define an air flow space between said section of the closed loop flow path and said sample holder on each of the opposite sides of the sample holder.

7. The method according to claim 1, wherein the air velocity through said section of the closed loop flow path is 10–30 m/sec.

8. The method according to claim 1, wherein said electrical heater is of annular configuration circumscribing a portion of said closed loop flow path.

9. The method according to claim 1, wherein said sample holder includes a plurality of metal tubes arranged in a rectangular matrix array for receiving the samples.

10. The method according to claim 1, wherein the section of said closed loop flowpath into which the sample holder is introduced is of decreasing cross-sectional area from the upstream side of said sample holder to the downstream side of the sample holder, to produce an increase in the velocity of the airflow at said downstream side as compared to that at said upstream side.

11. The method according to claim 10, wherein said decreasing cross-sectional area is effected by the provision of an inclined baffle in said section of the closed loop flow path into which the sample holder is introduced, said inclined baffle underlying said sample holder.

12. The method according to claim 10, wherein said decreasing cross-sectional area is effected by mounting the sample holder in an inclined position in said section of the closed loop flowpath.

13. Apparatus for effecting rapid thermal cycling of samples, comprising:

a housing including a channel defining a closed loop flow path for air;

an impeller within said housing for producing a high velocity laminar air flow through said closed loop flow path;

an electrical heater within said housing for heating the air flowing through said closed loop flow path to a desired temperature;

an access opening in a section of said channel for introducing a sample holder containing at least one sample into a sample compartment in said closed loop flow path for exposure to the high-velocity heated air flowing therethrough; and a control means for selectively energizing the electrical heater to rapidly heat said sample by the heated air flowing through the closed loop flowpath, and for selectively de-energizing the electrical heater and opening the closed loop flow path with respect to the atmosphere to rapidly cool said sample.

14. The apparatus according to claim 13, wherein said section of the channel into which the sample holder is introduced is of rectangular cross section.

15. The apparatus according to claim 13, wherein said channel comprises a first section including first and second legs parallel to each other and joined by a first U-shaped juncture, and a second section including third and fourth legs parallel to each other and joined by a second U-shaped juncture;

said first and second legs of the first section being perpendicularly joined to said third and fourth legs of the second section to define a closed loop flow path constituted of two U-shaped loops perpendicularly joined to each other.

16. The apparatus according to claim 13, wherein said sample compartment has a bottom mat and includes a cover for pressing the sample-holder against the mat, the cover containing another electrical heater which may be energized during the process to reduce excessive vaporization of the samples.

17. The apparatus according to claim 13, wherein the section of the channel into which sample holder is introduced has a transverse dimensions slightly larger than that of said sample holder to define an air flowspace between said section of the channel and said sample holder on each of the opposite sides of the sample holder.

18. The apparatus according to claim 13, wherein said channel defining said closed loop flow path is a closed loop channel including an inlet opening leading from the atmosphere into said loop channel, an outlet opening leading from the closed loop channel to the atmosphere, and an actuator for selectively opening and closing at least said outlet opening.

19. The apparatus according to claim 18, wherein there is also an actuator for selectively opening and closing said inlet opening.

20. The apparatus according to claim 13, wherein said electrical heater is of annular configuration circumscribing a portion of said closed loop flow path.

21. The apparatus according to claim 13, wherein said electrical heater is positioned inside the channel upstream from the air impeller.

22. The apparatus according to claim 13, wherein said sample holder includes a plurality of metal tubes arranged in a rectangular matrix array for receiving the samples.

23. Apparatus for effecting rapid thermal cycling of samples, comprising: a housing including a channel defining a closed loop flow path for air;

an impeller within said housing for producing a high velocity air flow through said closed loop flow path;

an electrical heater within said housing for heating the air flowing through said closed loop flow path to a desired temperature;

an access opening in a section of said channel for introducing a sample holder containing at least one sample into a sample compartment in said closed loop flow path for exposure to the high-velocity heated air flowing therethrough;

and control means for selectively energizing the electrical heater to rapidly heat said sample by the heated air flowing through the closed loop flowpath, and for selectively de-energizing the electrical heater and opening the closed loop flow path with respect to the atmosphere to rapidly cool said sample;

the section of said closed loop flow path into which the sample holder is introduced being of decreasing cross-sectional area from the upstream side of said sample holder to the downstream side of the sample holder, to produce an increase in the velocity of the airflow at said downstream side as compared to that at said upstream side.

24. The apparatus according to claim 23, wherein said decreasing cross-sectional area is effected by including an inclined baffle in said section of the closed loop flow path into which the sample holder is introduced, said baffle underlying said sample holder.

25. The apparatus according to claim 23, wherein said decreasing cross-sectional area is effected by mounted the sample holder in an inclined position in said section of the closed loop flowpath.

26. The apparatus according to claim 23, wherein said impeller produces a high velocity laminar air flow through said closed loop flow path.

* * * * *